(12) United States Patent
Mitusina (10) Patent No.: US 8,057,500 B2
(45) Date of Patent: *Nov. 15, 2011

(54) FLEXIBLE INNER MEMBER HAVING A FLEXIBLE REGION COMPRISING A CUT WITH CONVOLUTED PATH AREAS

(75) Inventor: Miroslav Mitusina, Ruskin, FL (US)

(73) Assignee: B&M Precision, Inc., Ruskin, FL (US)

( * ) Notice: Subject to any disclaimer, the term of this patent is extended or adjusted under 35 U.S.C. 154(b) by 382 days.

This patent is subject to a terminal disclaimer.

(21) Appl. No.: 12/184,648

(22) Filed: Aug. 1, 2008

(65) Prior Publication Data

US 2010/0030217 A1   Feb. 4, 2010

(51) Int. Cl.
*A61B 17/14* (2006.01)

(52) U.S. Cl. .......................... 606/180; 606/79; 606/170

(58) Field of Classification Search .................. 606/167, 606/170, 180, 79; 623/1.15
See application file for complete search history.

(56) References Cited

U.S. PATENT DOCUMENTS

| | | | |
|---|---|---|---|
| 4,646,738 A | 3/1987 | Trott | |
| 5,152,744 A | 10/1992 | Krause et al. | |
| 5,286,253 A | 2/1994 | Fucci | |
| 5,322,505 A | 6/1994 | Krause et al. | |
| 5,437,630 A | 8/1995 | Daniel et al. | |
| 5,510,070 A | 4/1996 | Krause et al. | |
| 5,529,580 A | 6/1996 | Kusunoki et al. | |
| 5,540,708 A | 7/1996 | Lim et al. | |
| 5,620,415 A | 4/1997 | Lucey et al. | |
| 5,620,447 A | 4/1997 | Smith et al. | |
| 6,033,433 A * | 3/2000 | Ehr et al. | 623/1.16 |
| 6,053,922 A | 4/2000 | Krause et al. | |
| 6,533,749 B1 | 3/2003 | Mitusina et al. | |
| 6,656,195 B2 * | 12/2003 | Peters et al. | 606/159 |
| 7,276,074 B2 | 10/2007 | Adams et al. | |
| 7,338,495 B2 | 3/2008 | Adams | |
| 2005/0090849 A1 | 4/2005 | Adams | |

FOREIGN PATENT DOCUMENTS

DE   3828478 A1   5/1989

* cited by examiner

*Primary Examiner* — Elizabeth Houston
*Assistant Examiner* — Sarah Webb (57) ABSTRACT

A flexible inner member for rotation within an angled outer tubular member of a rotary tissue cutting instrument to cut anatomical tissue includes a flexible region for conforming to the configuration of an angled region of the outer tubular member. The flexible region comprises a cut having convoluted path areas formed through a cylindrical wall of a tubular body of the inner member. The convoluted path areas are rotationally spaced on the tubular body in alternating sequence with connecting path segments of the cut. The cut follows a convoluted path in the convoluted path areas forming the wall of the tubular body into a pair of complementary, mating hook formations of opposed curvature. The connecting path segments extend rotationally along the tubular body between the convoluted path areas.

19 Claims, 3 Drawing Sheets

FLEXIBLE INNER MEMBER HAVING A FLEXIBLE REGION COMPRISING A CUT WITH CONVOLUTED PATH AREAS

BACKGROUND OF THE INVENTION

1. Field of the Invention

The present invention pertains generally to flexible inner members rotatably disposed within angled outer tubular members of rotary surgical tissue cutting instruments wherein the inner member has a flexible region to transmit torque while conforming to the angled configuration of the outer tubular member. More particularly, the present invention pertains to flexible inner members of angled rotary tissue cutting instruments wherein the flexible region comprises a cut with convoluted path areas formed in a tubular body of the inner member.

2. Brief Discussion of the Related Art

Angled rotary tissue cutting instruments have become widely accepted for use in various surgical procedures to cut anatomical tissue at a surgical site within a patient's body. Angled rotary tissue cutting instruments typically comprise an elongate angled outer tubular member and an elongate flexible inner tubular member rotatably disposed within the angled outer tubular member. A cutting element at a distal end of the inner member is exposed from an opening at a distal end of the outer member to cut anatomical tissue at the surgical site when the inner member is rotated within the outer member. The inner member is ordinarily rotated within the outer member via a powered surgical handpiece coupled to proximal ends of the outer and inner members, with the handpiece being maintained externally of the patient's body. The outer tubular member has one or more angled, curved or bent regions along its length to provide an angled configuration that facilitates positioning of the cutting element at the surgical site when the instrument is introduced in the patient's body, and particularly when the instrument is introduced through a narrow or small size, natural or artificially created entry opening in the patient's body. The inner tubular member is provided with one or more flexible regions to reside within the one or more angled, curved or bent regions of the outer member for transmitting torque to rotate the cutting element while conforming to the angled configuration of the outer member. The angled configuration of the outer member is particularly beneficial in facilitating positioning of the cutting element at the surgical site where there is a non-straight path in the body from the entry opening to the surgical site. In such cases, angled rotary tissue cutting instruments are usually better suited to access the surgical site more easily and quickly, and with less trauma to the patient, than are rotary tissue cutting instruments in which the outer tubular member is longitudinally straight. In many surgical procedures performed using rotary tissue cutting instruments, the internal lumen of the inner tubular member is used to transmit suction to the surgical site to aspirate anatomical tissue and/or fluid through the inner member. In addition, an annular gap or clearance between the internal diameter of the outer member and the external diameter of the inner member is commonly used as an irrigation passage to supply irrigation fluid to the surgical site.

One design advantage in rotary tissue cutting instruments is to minimize the external diametric size of the outer member to allow introduction of the instrument in the patient's body through entry openings as small as possible in size and/or to facilitate advancement of the instrument to the surgical site with as little trauma as possible to the patient. Another design advantage in rotary tissue cutting instruments is to maximize the internal diameter of the inner tubular member so that aspiration of tissue and/or fluid through the inner member can be accomplished with greater efficiency and with less risk of clogging. Yet a further design advantage in rotary tissue cutting instruments is to maintain an appropriate annular clearance between the internal diameter of the outer tubular member and the external diameter of the inner member to avoid jamming of the instrument and/or to provide efficient flow of irrigation fluid between the outer and inner members. In angled rotary tissue cutting instruments, it would also be a design advantage to minimize the number of structural components or parts required for the flexible region of the inner member, thereby reducing manufacturing and material costs, as well as reducing the risk of operational problems arising from structural complexity and/or multiple structural components. The foregoing design advantages must necessarily be balanced against the need to maintain sufficient strength and rigidity in the flexible inner members of angled rotary tissue cutting instruments when transmitting torque via the flexible regions, particularly considering that angled rotary tissue cutting instruments must oftentimes be designed to operate at high rotational speeds and to withstand the forces imposed when cutting very hard or tenacious anatomical tissue.

Various designs previously proposed for the flexible regions in the inner members of angled rotary tissue cutting instruments have limited the extent to which the aforementioned design advantages can be optimized in angled rotary tissue cutting instruments. Some of the deficiencies associated with prior designs proposed for the flexible regions in the inner members of angled rotary tissue cutting instruments include increased radial thickness of the annular wall of the inner tubular member along the flexible region resulting in a larger external diameter and/or smaller internal diameter for the inner member, structural complexity and/or the need for multiple assembled structural parts to form the flexible region, constriction of the internal diameter of the flexible region when transmitting torque within an angled region of the outer tubular member, longitudinal stretching of the flexible region, and insufficient strength and rigidity in the flexible region limiting the range of bend angles over which the flexible region is able to effectively transmit torque. Designs for the flexible regions of inner tubular members of angled rotary tissue cutting instruments that result in the inner tubular member being of larger external diametric size normally require that the angled outer tubular member be of larger external diametric size in order to rotatably receive the inner member while maintaining the appropriate annular clearance between the outer and inner members. Designs for the flexible regions of inner tubular members of angled rotary tissue cutting instruments that result in the inner tubular member having a smaller internal diameter or that result in constriction of the internal diameter will typically have a negative impact on the ability to aspirate tissue and/or fluid through the inner tubular member. Designs for the flexible regions of inner tubular members of angled rotary tissue cutting instruments that involve structural complexity and/or multiple assembled structural parts generally result in the inner tubular member being of higher cost and at increased risk of operational problems. Operational problems are also more likely to occur in inner tubular members of angled rotary tissue cutting instruments in which the design for the flexible region in the inner member makes the flexible region prone to longitudinal stretching.

In some flexible inner tubular members of angled rotary tissue cutting instruments, the flexible regions are formed of a plurality of concentric spirals, typically an inner spiral, a middle spiral and an outer spiral attached to one another at their ends. Each spiral is formed by winding a flat strip of material, with alternating spirals being wound in opposite rotational directions about a central longitudinal axis of the inner member as represented by U.S. Pat. No. 4,646,738 to Trott, U.S. Pat. No. 5,286,253 to Fucci and U.S. Pat. No. 5,540,708 to Lim et al. It has also been proposed to provide shafts having flexible regions made up of concentric coils of wound wire of circular cross-section, rather than wound flat strips of material, as represented by U.S. Pat. No. 5,437,630 to Daniel et al and U.S. Pat. No. 5,529,580 to Kusunoki et al and by German Patent DE 3828478 A1. The radial dimension or thickness of the annular wall of a flexible region comprised of multiple concentric spirals or coils tends to be substantial since it includes the individual thickness of each spiral or coil. Flexible regions of this type tend to result in flexible inner tubular members of larger external diametric sizes requiring diametrically larger outer tubular members, and/or of smaller internal diameters leading to reduced aspiration capability. In addition, flexible inner tubular members having these types of flexible regions will ordinarily be associated with higher material costs due to the multiple structural components involved and with higher manufacturing costs associated with producing and assembling the different structural components. The risk of operational problems may be greater due to the presence of multiple structural components and increased structural complexity, and the securement or attachment sites for the multiple spirals or coils present the potential for structural failure.

Another design approach for the flexible regions in the flexible inner tubular members of angled rotary tissue cutting instruments involves a single continuous spiral or helical cut formed in an inner tube, and one or more layers of spiral wrap disposed over the cut region of the inner tube as represented by U.S. Pat. No. 6,533,749 B1 to Mitusina et al and U.S. Pat. No. 6,656,195 B2 to Peters et al, and by United States Patent Application Publication No. US2005/0090849 A1 to Adams. The one or more layers of spiral wrap are each formed by winding a flat strip of material over the cut region in the inner tube and attaching the ends of the strip to the tube. The helical cut and the one or more layers of spiral wrap are arranged so that their rotational direction or turn about a central longitudinal axis of the inner member alternate in opposite directions. The Peters et al patent discloses the helical cut in the inner tube as having a dovetail pattern. The extent to which it is possible to minimize the radial dimension or thickness of the annular wall of a flexible region comprised of an inner tube and one or more layers of spiral wrap over a cut region of the tube is limited by the fact that the wall thickness of the inner tube and the thickness of each layer of spiral wrap contribute cumulatively to the radial dimension of the annular wall formed by the flexible region. Furthermore, the inner tube and each spiral wrap are separate structural components assembled during manufacture, giving rise to issues of increased cost and structural complexity.

U.S. Pat. No. 7,338,495 B2 to Adams is an example of a flexible region in a flexible inner tubular member of an angled rotary surgical cutting instrument formed of a helical cut in an inner tube, a layer of adhesive disposed over the cut region of the inner tube, and a heat shrunk sleeve disposed over the cut region of the inner tube and being bonded thereto by the adhesive. The helical cut is formed in the inner tube in a stepped pattern. Again, the radial thickness of the annular wall formed by the flexible region is made up of the individual thicknesses of the inner tube wall, the adhesive layer, and the wall of the sleeve. The flexible region requires multiple parts or materials in addition to the inner tube, and is still somewhat complicated from a manufacturing standpoint.

Flexible regions have also been provided in the inner tubular members of angled rotary tissue cutting instruments by forming disconnected slots or openings in an inner tube as illustrated by U.S. Pat. No. 5,152,744, 5,322,505 and 5,510,070 to Krause et al, U.S. Pat. No. 5,620,415 to Lucey et al, and U.S. Pat. No. 5,620,447 to Smith et al. Each slot is filled with a pliable material in a multi-step process carried out after the slots are formed. The preferred slot configuration described in the Krause et al, Lucey et al and Smith et al patents involves circumferentially discontinuous slots disposed in parallel spaced relation, the slots being arranged perpendicular to the longitudinal axis of the inner tube.

U.S. Pat. No. 6,053,922 to Krause et al pertains to a flexible shaft for reaming the medullary space in bones. In contrast to the flexible inner members of angled rotary tissue cutting instruments, the flexible shaft of Krause et al '922 is not shown to be rotatably disposed within a rigid outer tubular member, and is thusly not subject to the same design considerations as the inner members of rotary tissue cutting instruments and of angled rotary tissue cutting instruments in particular. In further distinction to the flexible inner tubular members of angled rotary tissue cutting instruments, the flexible shaft of Krause et al '922 is said to be an elongated tubular member of substantial wall thickness. A flexible inner tubular member of substantial wall thickness would be undesirable in an angled rotary tissue cutting instrument because it would result in a reduction in the internal diameter of the inner member, which would reduce aspiration capability, and/or it would require an outer member of larger external diameter to accommodate the inner member, which would require larger size entry openings in the patient's body for introduction of the instrument. The tubular member of Krause et al '922 comprises a slot, said to be of substantial width, extending spirally around the tubular member in a pattern that forms pairs of complementary, mating interlocking teeth and recesses in the tubular member that Krause et al '922 relies on to transmit torque. The tooth and recess slot pattern repeats without interruption, such that each complementary, mating interlocking tooth and recess pair borders the next complementary, mating interlocking tooth and recess pair. The slot configuration thusly consists entirely of the configurations of the teeth and recesses of the particular slot pattern, resulting in an "unbound joint".

Despite the numerous different design approaches previously proposed for the flexible inner members of angled rotary tissue cutting instruments, it was not recognized until the present invention that a flexible region comprising a cut formed in a tubular body of the inner member with convoluted path areas between non-convoluted connecting path segments of the cut would provide numerous design advantages, including the advantages of design simplicity, eliminating the need for the flexible region to include an additional structure or layer of material over the cut region of the tubular body or within the cut itself, appropriate rigidity and torsional strength, resistance to stretching in the longitudinal axial direction of the inner member, preservation of the integrity of the internal diameter of the inner member, and the capability to transmit torque within angled outer tubular members having a broad range of bend angles.

SUMMARY OF THE INVENTION

The present invention is generally characterized in a flexible inner member for being rotatably disposed within an angled outer tubular member of a rotary tissue cutting instrument. The outer tubular member includes a distal end, a longitudinal internal passage, an open proximal end communicating with the passage, an angled region between the distal and proximal ends, and an opening in the distal end communicating with the internal passage. The flexible inner member has a distal end, a proximal end, a tubular body between the distal and proximal ends of the inner member, a cutting element at the distal end of the inner member, and a flexible region for being disposed within the angled region of the outer tubular member. When the inner member is rotatably disposed within the internal passage of the outer tubular member, the cutting element is exposed from the opening in the outer tubular member, and the flexible region is disposed within the angled region to transmit torque to rotate the cutting element while conforming to the configuration of the angled region. The tubular body of the inner member has a central longitudinal axis and a cylindrical wall having a wall thickness between external and internal diameter surfaces of the cylindrical wall. The flexible region comprises a convoluted or vortical cut in the tubular body extending entirely through the wall thickness of the cylindrical wall. The convoluted cut has a starting end on the tubular body and has a terminating end on the tubular body. The convoluted cut extends longitudinally along the tubular body and extends in a rotational direction about the central longitudinal axis in a forward direction of the convoluted cut from the starting end to the terminating end. The convoluted cut includes a plurality of convoluted or vortical path areas rotationally spaced about the central longitudinal axis between the starting end and the terminating end and in which the cut follows a convoluted or vortical path or configuration, and a plurality of connecting path segments in alternating sequence or succession with the convoluted path areas between the starting end and the terminating end. The connecting path segments extend rotationally along the tubular body in the rotational direction of the cut about the central longitudinal axis. The connecting path segments are devoid of convoluted path areas and extend in the rotational direction at a non-perpendicular angle to the central longitudinal axis.

The convoluted path areas are situated between a next preceding connecting path segment and a next succeeding connecting path segment in the forward direction of the cut. The convoluted path followed by the cut in the convoluted path areas comprises a first major curve of concave curvature extending in a lateral direction away from the next preceding connecting path segment, a first minor curve of concave curvature reverse from the curvature of the first major curve and extending from the first major curve in the opposite lateral direction toward the next preceding connecting path segment, a second minor curve of concave curvature reverse from the curvature of the first minor curve and extending from the first minor curve in the lateral direction toward the next preceding connecting path segment, and a second major curve of concave curvature reverse from the curvature of the second minor curve and extending from the second minor curve in the lateral direction away from the next preceding connecting path segment to join the next succeeding connecting path segment. The first minor curve is within the second major curve and is spaced from the second major curve in a direction radial to the second major curve. The second minor curve is within the first major curve and is spaced from the first major curve in a direction radial to the first major curve.

The configuration of the cut in the convoluted path areas forms the wall of the tubular body into a pair of complementary, mating and interengaging, opposed first and second hook formations in the convoluted path areas. The first hook formations have a concavely curving body ending at a rounded tip. The second hook formations have a concavely curving body ending at a rounded tip, the body of the second hook formation being of reverse curvature from the body of the first hook formation. The tip of each of the first and second hook formations mates with the concave curvature of the body of the opposed hook formation.

DETAILED DESCRIPTION OF THE INVENTION

Figure 1:
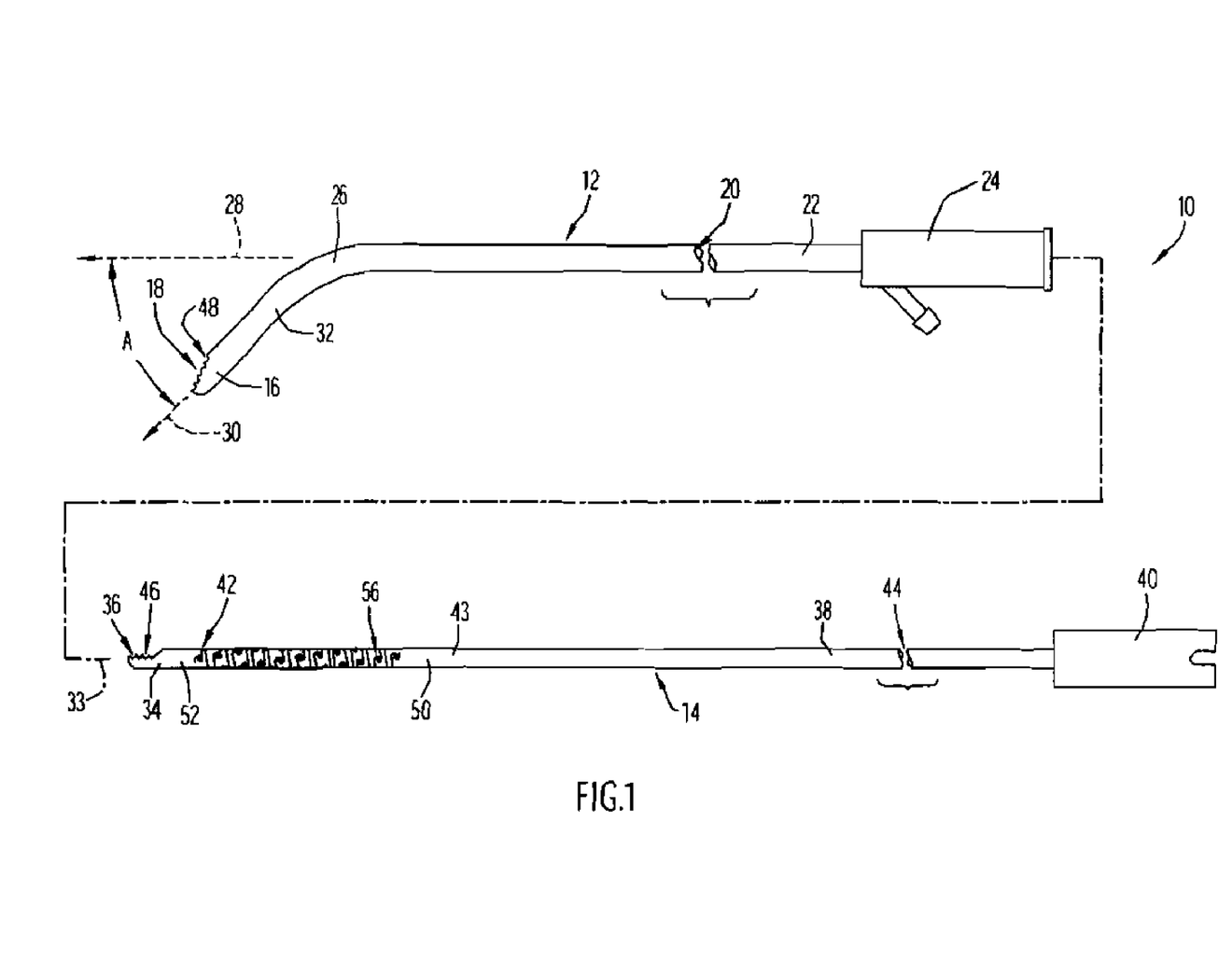
FIG. 1 is an exploded side view of an angled rotary tissue cutting instrument.

An angled rotary tissue cutting instrument 10 is depicted in FIG. 1 and comprises an elongate angled outer tubular member 12 and an elongate flexible inner member 14 for being rotatably disposed within the outer tubular member 12. The outer tubular member 12 has a distal end 16 with an opening 18 therein in communication with the internal passage 20 in the outer tubular member. The outer tubular member 12 has a proximal length portion 22 terminating at an open proximal end typically secured in an outer member hub 24 designed for engagement with a powered surgical handpiece (not shown) in a conventional manner. The outer tubular member 12 is provided with one or more angled, curved or bent regions 26 along the length thereof, such that the outer tubular member 12 has an angled configuration. Each angled region 26 in the outer tubular member 12 defines a bend angle A corresponding to the angle defined between length portions of the outer tubular member 12 that are joined by the angled region. The outer tubular member 12, for example, has a bend angle A defined between the central longitudinal axis 28 of the proximal length portion 22 of the outer member 12 and a central longitudinal axis 30 of a distal length portion 32 of the outer member 12 which is joined to the proximal length portion 22 by the angled region 26. The size and the direction of the bend angle A can vary individually for each angled region 26. The outer tubular member 12 illustrated in FIG. 1 has one angled region 26 with a bend angle A extending in a downward direction from proximal length portion 22.

As a result of its angled configuration, the outer tubular member 12 is not longitudinally straight along its length. However, the outer tubular member 12 can initially be provided in a longitudinally straight configuration, without the one or more angled regions 26, and can be bent from the longitudinally straight configuration in any suitable manner to obtain the angled configuration desired for the outer tubular member. Accordingly, bending the outer tubular member 12 from the longitudinally straight configuration to the desired angled configuration will involve bending the outer tubular member 12 as needed to obtain the desired number of angled regions 26 at the desired location or locations along the length of the outer tubular member and extending in the desired direction or directions at the desired bend angle or angles A. It should be appreciated that the outer tubular member 12 can be bent from the longitudinally straight configuration to the angled configuration with or without the flexible inner member 14 disposed within the outer tubular member 12. The outer tubular member 12 is rigid in a longitudinally straight configuration but is able to be bent to form the desired angled region(s) when sufficient bending force is applied. The outer tubular member 12 is or remains rigid after bending to form the one or more angled regions.

The inner member 14 has a central longitudinal axis 33, a distal end 34 provided with or formed as a cutting element 36, a proximal length portion 38 terminating at a proximal end that is typically secured in an inner member hub 40, and one or more flexible regions 42 between the cutting element 36 and the inner member hub 40. The one or more flexible regions 42 impart flexibility to the inner member that allows the inner member to bend along its central longitudinal axis 33. When the inner member 14 is assembled with the outer tubular member 12 to cut anatomical tissue, the inner member 14 will extend through the outer member hub 24 and will be rotatably disposed within the internal passage 20 of the outer tubular member 12 with the cutting element 36 exposed from the opening 18 in the outer member, with the one or more flexible regions 42 disposed within the one or more angled regions 26 of the outer member, and with the inner member hub 40 disposed proximally of the outer member hub 24 for engagement with the powered surgical handpiece. The powered surgical handpiece is operated in a conventional manner to rotate the inner member 14 relative to and within the outer tubular member 12, and the one or more flexible regions 42 transmit torque to rotate the cutting element 36 while conforming to the angled configuration of the outer tubular member 12. As the inner member 14 is rotated within the outer tubular member 12, the cutting element 36 exposed from the opening 18 will cut anatomical tissue contacted with the cutting element 36.

The inner member 14 comprises a cylindrical tubular body 43 coaxial with the central longitudinal axis 33 and having an internal lumen 44 extending longitudinally within the tubular body. The tubular body 43 preferably has an open end forming the proximal end of the inner member 14 and preferably extends from the proximal end of the inner member 14 to the cutting element 36, which is the case for tubular body 43. Preferably, the tubular body 43 is an integral and unitary or monolithic tube from the proximal end of the inner member 14 to the cutting element 36, which is also the case for tubular body 43. Accordingly, the flexible inner member 14 is a flexible inner tubular member. As described further below, the one or more flexible regions 42 are each formed by a convoluted or vortical cut in the tubular body 43.

The cutting element 36 can have various cutting configurations effective to cut anatomical tissue including the various cutting configurations conventionally used for the inner members of rotary tissue cutting instruments. The cutting element 36 can be a structure that is hollow or provided with an interior cavity or channel in communication with the lumen 44 of the tubular body 43. The cutting element 36 can be a structure formed separate from and attached to the tubular body 43. The distal end 34 of the inner tubular member 14 can have an opening 46 therein in communication with the internal lumen 44 of the inner member 14, and the opening 46 can communicate with the lumen 44 via the interior cavity or channel in the structure that forms the cutting element 36. The cutting configuration for the cutting element 36 can include one or more cutting surfaces or edges along the periphery of the opening 46 as is the case for the cutting element 36 of the inner member 14 depicted in FIG. 1. The cutting surfaces or edges of the cutting element 36 can be defined by cutting tooth formations, as is also the case for the cutting element 36 of inner member 14. The cutting surfaces or edges of the cutting element 36 can be defined by flute formations as in a bur tip, for example.

The distal end 16 of the outer tubular member 12 can be provided with or formed as a cutting element 48 that cooperates with the cutting element 36 of the inner member 14 to cut anatomical tissue. The cutting element 48 can have various cutting configurations effective to cut anatomical tissue in cooperation with the cutting element 36, and the various cutting configurations conventionally used for the outer members in rotary tissue cutting instruments can be used for the cutting configuration of the cutting element 48. The cutting configuration for the cutting element 48 can include one or more cutting surfaces or edges along the periphery of the opening 18 as is the case for the cutting element 48 of the outer tubular member 12 depicted in FIG. 1. The cutting surfaces or edges of the cutting element 48 can be defined by cutting tooth formations, as is also the case for the cutting element 48. Typically, the cutting elements 36 and 48 cooperate to cut anatomical tissue as a result of rotation of the one or more cutting surfaces or edges of the cutting element 36 past the one or more cutting surfaces or edges of the cutting element 48.

As the cutting element 36 is rotated, the opening 46 in the inner member 14 will come into alignment with the opening 18 in the outer tubular member 12, allowing anatomical tissue and/or fluid to enter the lumen 44 of the inner member 14 through the aligned openings 18 and 46. Through the application of vacuum or suction to the lumen 44, typically via a connection at a proximal end of the instrument 10 in a conventional manner, the lumen 44 can serve as an aspiration passage by which suction is applied at the surgical site via the aligned openings 18 and 46 and by which fluid and/or anatomical tissue is/are drawn into the lumen 44 through the aligned openings 18 and 46 for evacuation through the instrument 10.

In order for the inner member 14 to rotate within the outer tubular member 12 without jamming, an appropriate annular clearance or gap is present between the internal diameter of the outer tubular member 12 and the external diameter of the inner member 14 when the members 12 and 14 are assembled to cut tissue. The annular clearance or gap between the outer and inner members 12 and 14 can serve as an irrigation passage by which irrigation fluid supplied to the annular clearance, typically from a proximal end of the instrument 10, is conveyed distally and released at the surgical site through the opening 18 in the outer tubular member 12.

The inner member 14 can have a single flexible region 42 of sufficient length and at the appropriate location to reside in and conform to the configuration of one or more angled regions 26 in the outer tubular member 12. The inner member 14 can have a plurality of flexible regions 42, each of sufficient length and at the appropriate location to reside in and conform to the configuration of a corresponding angled region 26 in the outer tubular member 12. Each flexible region 42 can be disposed adjacent and/or between rigid or non-flexible length segments of the tubular body 43. The inner member 14 is an example of one having a single flexible region 42 disposed between rigid or non-flexible length segments 50 and 52 of the tubular body 43, the single flexible region 42 being located appropriately along the length of the inner member 14 to reside within the single angled region 26 in the outer tubular member 12 and being of sufficient length to conform to the configuration of the single angled region 26 when the inner member 14 is assembled with the outer member 12 to cut anatomical tissue. The length segment 50 of the tubular body 43 is part of the proximal length portion 38, which will be disposed within the proximal length portion 22 of the outer member 12 when the inner member is assembled with the outer member to cut anatomical tissue. The length segment 52 of the tubular body 43 may thusly be considered a distal length portion and will be disposed within the distal length portion 32 of the outer member 12 when the inner and outer members are assembled to cut anatomical tissue.

Figure 2:
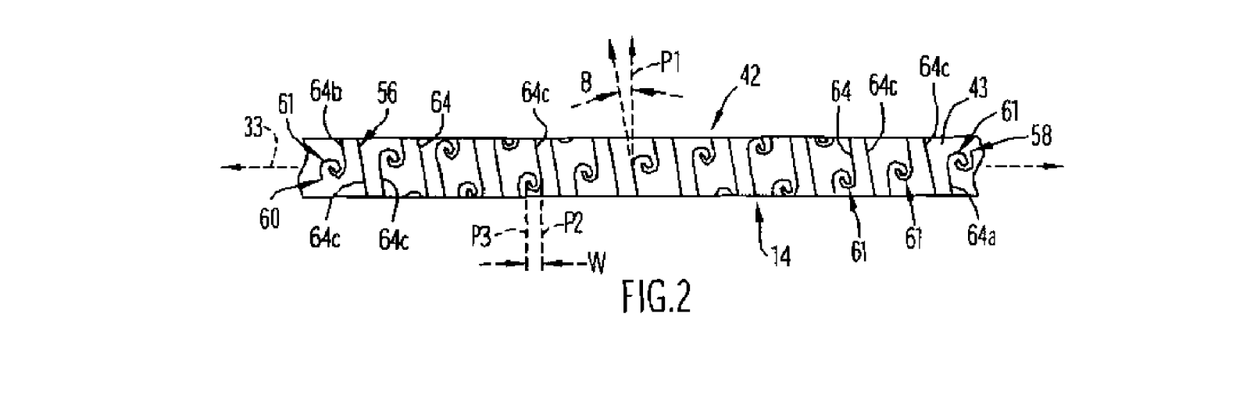
FIG. 2 is a broken side view of a flexible region of a flexible inner member of the angled rotary tissue cutting instrument.
Figure 3:
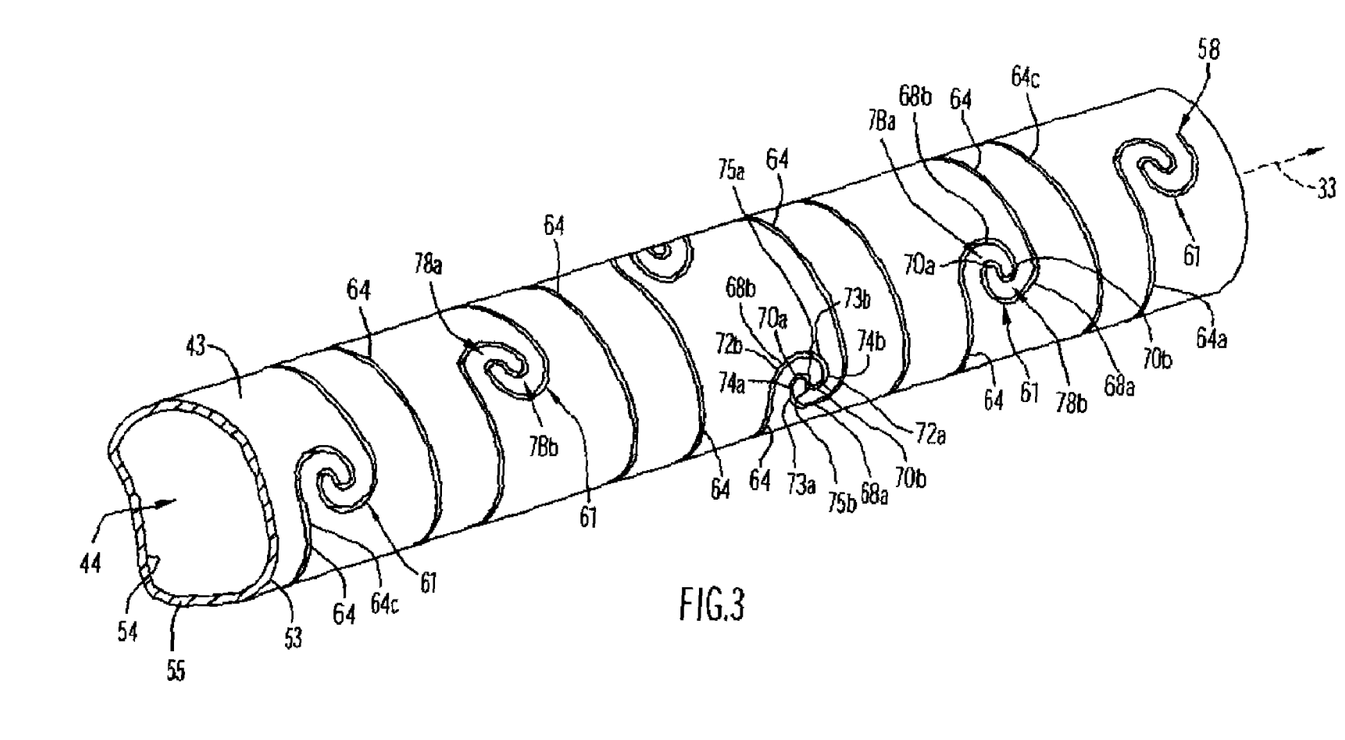
FIG. 3 is a broken perspective view of a tubular body having a convoluted cut therein comprising the flexible region of FIG. 2.
Figure 4:
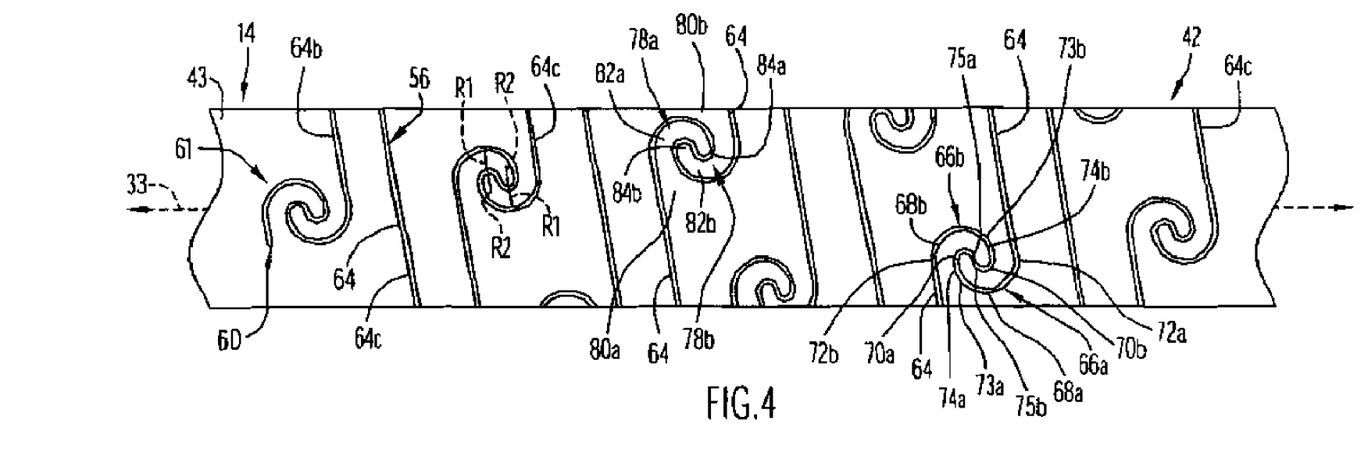
FIG. 4 is a broken, enlarged side view of the convoluted cut in the tubular body.

The flexible region 42, which is best depicted in FIGS. 2-4, comprises a convoluted or vortical cut 56 formed in the tubular body 43 of the inner member 14. As best shown in FIG. 3, the tubular body 43 has a cylindrical wall with an external diameter surface 53, an internal diameter surface 54 defining the lumen 44, and a radial wall thickness 55 between the external and internal diameter surfaces. Prior to the convoluted cut 56 being formed therein, the wall of the tubular body 43 along the flexible region 42 and along the length segments 50 and 52 is a rigid, integral and unitary, one piece or monolithic, solid, annular wall coaxial with the central longitudinal axis 33. The convoluted cut 56 extends through the entire wall thickness 55 of the cylindrical wall of the tubular body 43. The convoluted cut 56 has a starting end 58 on the tubular body 43 as seen in FIGS. 2 and 3, and has a terminating end 60 on the tubular body 43 as seen in FIGS. 2 and 4. The cut 56 extends longitudinally along the tubular body 43 and extends in a rotational direction about the central longitudinal axis 33 in a forward direction of the cut 56, the forward direction being the direction of advancement or forward progress followed by the path of the cut from the starting end 58 to the terminating end 60. The cut therefore follows a winding path from the starting end to the terminating end. Looking in the forward direction of cut 56 from the starting end 58 toward the terminating end 60, the rotational direction for cut 56 is in a counterclockwise direction about the axis 33 from the starting end 58 to the terminating end 60. However, it should be appreciated that the cut could rotate in a clockwise rotational direction about the axis 33 in the forward direction from the starting end 58 toward the terminating end 60. The convoluted cut 56 has a plurality of convoluted or vortical path areas 61 between the starting end 58 and the terminating end 60 within which the cut 56 follows a convoluted or vortical path or configuration as explained further below. In the case of convoluted cut 56, the terminating end 60 is located on the tubular body 43 distally of the starting end 58, such that the forward direction of the cut 56 is in the distal direction along the inner member 14. It should be appreciated, however, that the starting and terminating ends can be reversed, such that the end 60 can be the starting end for the cut 56 and the end 58 can be the terminating end for the cut 56, in which case the forward direction of the cut is in the proximal direction along the inner member 14.

The convoluted cut 56 comprises the plurality of convoluted path areas 61, which are rotationally spaced about the central longitudinal axis 33, and a plurality of connecting path segments 64 in alternating sequence or succession with the convoluted path areas 61 between the starting end 58 and the terminating end 60. The convoluted cut 56 is continuous within and through each convoluted path area 61, there being no breaks or gaps in the cut 56 in the convoluted path areas 61. The convoluted cut 56 is one in which the entire cut 56 is continuous from its starting end 58 to its terminating end 60, there being no breaks or gaps in the cut 56 from the starting end to the terminating end.

The connecting path segments 64 for the convoluted cut 56 comprise a starting connecting path segment 64a adjacent the starting end 58, a terminating connecting path segment 64b adjacent the terminating end 60, and a plurality of intermediate connecting path segments 64c between the starting and terminating connecting path segments 64a and 64b. The connecting path segments 64 extend rotationally about the central longitudinal axis 33 in the rotational direction of the cut 56, i.e. counterclockwise in the case of convoluted cut 56. The connecting path segments 64 extend rotationally about the central longitudinal axis 33 at a non-perpendicular angle B to the central longitudinal axis 33. As seen in FIG. 2, the connecting path segments 64 extend rotationally along the tubular body 43 at an acute angle B to a plane P1 perpendicular to the central longitudinal axis 33. In the case of convoluted cut 56, the connecting path segments 64 extend in the forward direction of the cut 56 with an angle or slant toward the proximal end or direction of the inner member 14 and toward the starting end 58 of the cut 56. The connecting path segments 64 are non-convoluted or devoid of convoluted path areas 61. The connecting path segments 64 may each follow a linear course or path that is disposed in a plane that defines angle B with the plane P1. The connecting path segments 64 are of the same length between the convoluted path areas 61 such that the convoluted path areas 61 repeat at uniform intervals along the cut 56.

The starting connecting path segment 64a extends rotationally along the tubular body 43 in the forward direction of the cut 56 to a convoluted path area 61 situated between the starting connecting path segment 64a and a first intermediate connecting path segment 64c, the first intermediate connecting path segment 64c being the connecting path segment 64 that next succeeds or follows the starting connecting path segment 64a in the forward direction of the cut 56. Each intermediate connecting path segment 64c extends rotationally along the tubular body 43 in the forward direction of the cut 56 from a convoluted path area 61 to a next succeeding convoluted path area 61. The terminating connecting path segment 64b extends rotationally along the tubular body 43 in the forward direction of the cut 56 from a convoluted path area 61 situated between the terminating connecting path segment 64b and a last intermediate connecting path segment 64c, the last intermediate connecting path segment 64c being the connecting path segment 64 that next precedes or comes before the terminating connecting path segment 64b. In other words, the last intermediate connecting path segment 64c is the connecting path segment 64 that next follows or comes after the terminating connecting path segment 64b in the reverse or rearward direction of the cut 56, the reverse direction of the cut 56 being in the opposite direction from the forward direction of the cut 56.

The convoluted cut 56 is an example of one in which the starting end 58 is a starting point of the cut 56 situated at the beginning of a convoluted path area 61 that next precedes the starting connecting path segment 64a and from which the starting connecting path segment 64a extends in the forward direction of the cut to a next succeeding convoluted path area 61. In this case, the first convoluted path area 61 of the cut 56 is the one at the starting end 58, and the starting connecting path segment 64a extends in the forward direction of the cut 56 from the first convoluted path area to the next succeeding convoluted path area. However, it should be appreciated that the convoluted cut 56 can be without a convoluted path area at the starting end 58 and that the starting end 58 can be a starting point of the cut 56 that begins the starting connecting path segment 64a. In this case, the convoluted path area 61 that next succeeds the starting connecting path segment 64a and to which the starting connecting path segment 64a extends in the forward direction of the cut 56 from the starting end 58 will be the first convoluted path area of the cut. The convoluted cut 56 is also an example of one in which the terminating end 60 is a terminal point of the cut 56 situated at the end of a convoluted path area 61 that next succeeds the terminating connecting path segment 64b and to which the terminating connecting path segment 64b extends in the forward direction of the cut 56 from a next preceding convoluted path area 61. In this case, the last convoluted path area 61 of the cut 56 is the one at the terminating end 60. It should be appreciated, however, that the convoluted cut 56 can be without a convoluted path area at the terminating end 60 and that the terminating end 60 can be a terminal point of the cut 56 at an end of the terminating connecting path segment 64b. In this case, the convoluted path area 61 that next precedes the terminating connecting path segment 64b and from which the terminating connecting path segment 64b extends in the forward direction of the cut to the terminating end 60 will be the last convoluted path areas of the cut 56. It should also be appreciated that the convoluted path area containing the starting end 58 and/or the terminating end 60 can be partial convoluted path areas in which the cut 56 follows less than the entire convoluted path followed by the cut in the other convoluted path areas 61.

The convoluted path or configuration defined or followed by the cut 56 in the convoluted path areas 61 is best described with reference to FIGS. 3 and 4 and includes an entering convoluted or vortical path portion 66a and an exiting convoluted or vortical path portion 66b. The entering convoluted path portion 66a is the path or configuration defined or followed by the cut 56 in the forward direction after entering the convoluted path area 61 from a next preceding connecting path segment 64, except that the convoluted path area that contains the starting end 58 is not preceded by a connecting path segment. The exiting convoluted path portion 66b is the path or configuration defined or followed by the cut 56 continuing in the forward direction from the entering convoluted path portion 66a to the next succeeding connecting path segment 64 upon exiting the convoluted path area 61, except that the convoluted path area that contains the terminating end 60 is not succeeded by a connecting path segment. The exiting convoluted path portion 66b is an inverted mirror image of the entering convoluted path portion 66a, and the convoluted path portions 66a and 66b together make up the entire or complete convoluted path or configuration followed by the cut 56 in the convoluted path area 61. However, as pointed out above, the convoluted path areas that contain the starting and/or terminating ends can have partial convoluted configurations. For example, the convoluted path area containing the starting end 58 can have an abbreviated or partial entering convoluted path portion, and the convoluted path area containing the terminating end 60 can have an abbreviated or partial exiting convoluted path portion.

The entering convoluted path portion 66a is a multi-directional, variably or multiply curving path or configuration comprising a first or entering path major curve 68a extending from the connecting path segment 64 that next precedes the convoluted path area 61, and a first or entering path minor curve 70a of reverse curvature to the major curve 68a and extending from the major curve 68a to the exiting convoluted path portion 66b. The exiting convoluted path portion 66b is a multi-directional, variably or multiply curving path or configuration comprising a second or exiting path minor curve 70b of reverse curvature to the first minor curve 70a and extending from the first minor curve 70a to a second or exiting path major curve 68b of the exiting convoluted path portion 66b. The major curve 68b of the exiting convoluted path portion 66b is of reverse curvature to the minor curve 70b and extends from the minor curve 70b to the connecting path segment 64. The first major curve 68a extends or curves in a lateral direction away from the next preceding connecting path segment 64 with a concave curvature, and the first minor curve 70a extends or curves from the first major curve 68a in the opposite lateral direction toward the next preceding connecting path segment 64 with a concave curvature opposite or reverse from the concave curvature of the first major curve 68a. The first major curve 68a is generally C-shaped or U-shaped in configuration with a mid-section between a pair of spaced apart sides. As best seen in FIGS. 3 and 4, the first major curve 68a includes an inner side 72a joined to, merging or continuous with the next preceding connecting path segment 64, and an outer side 73a joined to, merging or continuous with the first minor curve 70a. The first major curve 68a has a span or width between the inner and outer sides 72a and 73a. The first minor curve 70a is generally C-shaped or U-shaped in configuration with a mid-section between a pair of spaced apart sides, but has a more pronounced curvature than and curves in the opposite or reverse direction from the C-shaped or U-shaped configuration of the first major curve 68a. The first minor curve 70a has an outer side 74a joined to, merging or continuous with the outer side 73a of the first major curve 68a and has an inner side 75a continuous with the second minor curve 70b. The first major curve 68a has a major radius of curvature R1, and the first minor curve 70a has a minor radius of curvature R2 smaller than the major radius of curvature R1 as depicted in FIG. 4. The first minor curve 70a has a span or width between the outer and inner sides 74a and 75a that is less than the span of the first major curve 68a. The entering convoluted path portion 66a has a width W in a direction parallel to central longitudinal axis 33, the width W being the distance between plane P2 perpendicular to axis 33 and tangential to inner side 72a of major curve 68a and plane P3 parallel to plane P2 and tangential to outer side 74a of minor curve 70a.

The multi-directional, variably or multiply curving path or configuration of the entering convoluted path portion 66a is one in which the path of the cut 56 in the forward direction curves or extends in a lateral direction away from the next preceding connecting path segment 64 with a relatively gentle concave curvature (first major curve 68a) to an offset position spaced laterally from the next preceding connecting path segment 64, and then curves or extends with a reverse, relatively sharp or more pronounced concave curvature and in the opposite lateral direction (first minor curve 70a) toward the next preceding connecting path segment 64 to a second offset position mid-way between the first offset position and the next preceding connecting path segment 64. The lateral direction in which the first major curve 68a curves or extends away from the next preceding connecting path segment 64 is transverse to the next preceding and next succeeding connecting path segments and is the lateral direction toward the next succeeding connecting path segment 64. The opposite lateral direction in which the first minor curve 70a curves or extends from the first major curve 68a is transverse to the next preceding and next succeeding connecting path segments and is the lateral direction away from the next succeeding connecting path segment 64. The lateral direction and/or the opposite lateral direction can be perpendicular to the next preceding and next succeeding connecting path segments. The lateral direction that the first major curve 68a curves or extends away from the next preceding connecting path segment 64 is longitudinal along the tubular body 43 in the direction toward the terminating end 60 of the cut 56 and toward the distal end or direction of the inner member 14. The opposite lateral direction in which the first minor curve 70a curves or extends from the first major curve 68a is longitudinal along the tubular body 43 in the direction toward the starting end 58 of the cut 56 and toward the proximal end or direction of the inner member 14. The lateral direction and/or the opposite lateral direction may be longitudinal along the tubular body 43 parallel with the central longitudinal axis 33 or at an oblique angle to the central longitudinal axis 33.

The path or configuration of the exiting convoluted path portion 66b is the same multi-directional, variably or multiply curving path or configuration as the entering convoluted path portion 66a but is an inverted mirror image of the entering convoluted path portion 66a. The second minor curve 70b curves or extends laterally from the first minor curve 70a with a concave curvature opposite or reverse from the concave curvature of the first minor curve 70a and in the same lateral direction that the first minor curve 70a extends from the first major curve 68a, i.e. toward the next preceding connecting path segment 64 and away from the next succeeding connecting path segment 64. The second major curve 68b extends or curves laterally from the second minor curve 70b with a concave curvature opposite or reverse from the concave curvature of the second minor curve 70b and in the same lateral direction that the first major curve 68a extends from the next preceding connecting path segment, i.e. toward the next succeeding connecting path segment 64 and away from the next preceding connecting path segment 64, to join the next succeeding connecting path segment. The second minor curve 70b is generally C-shaped or U-shaped in configuration like the first minor curve 70a but is curved in the opposite or reverse direction from the C-shaped or U-shaped configuration of the first minor curve 70a. The second minor curve 70b is thusly curved in the same direction as the first major curve 68a. The second minor curve 70b has an outer side 74b, an inner side 75b joined to, merging or continuous with the inner side 75a of the first minor curve 70a, and a span between the outer and inner sides 74b and 75b as described for the first minor curve 70a. The second major curve 68b is generally C-shaped or U-shaped in configuration like the first major curve 68a but is curved in the opposite or reverse direction from the C-shaped or U-shaped configuration of the first major curve 68a. The second major curve 68b is thusly curved in the same direction as the first minor curve 70a. The second major curve 68b has an outer side 73b joined to, merging or continuous with the outer side 74b of the second minor curve 70b, an inner side 72b joined to, merging or continuous with the next succeeding connecting path segment 64, and a span between the inner and outer sides 72b and 73b as described for the first major curve 68a. The second major curve 68b has the radius of curvature R1, and the second minor curve 70b has the radius of curvature R2. In the convoluted path areas 61, the radius of curvature R2 is or is about 60% of the radius of curvature R1. The exiting convoluted path portion 66b has the same width W as the entering portion 66a but between parallel planes perpendicular to axis 33 and respectively tangential to the inner side 72b of second major curve 68b and to the outer side 74b of second minor curve 70b.

The first minor curve 70a is arranged within or inside of the second major curve 68b, with the curves 70a and 68b being in spaced relation and the span of the first minor curve 70a fitting within the span of the second major curve 68b. The first minor curve 70a is spaced from the second major curve 68b in a direction radial to the second major curve 68b. The second minor curve 70b is arranged within or inside of the first major curve 68a, with the curves 70b and 68a being in spaced relation and the span of the second minor curve 70b fitting within the span of the first major curve 68a. The second minor curve 70b is similarly but oppositely spaced from the first major curve 68a in a direction radial to the first major curve 68a. The arrangement and spaced relationship between curves 70b and 68a is the same as that for curves 70a and 68b, except that curves 70b, 68a are of opposite or reverse curvature from the curves 70a, 68b. The conjoined inner sides 75a, 75b of the first and second minor curves 70a, 70b are disposed mid-way or substantially mid-way between the outer sides 74a, 74b of the first and second minor curves 70a, 70b. The conjoined inner sides 75a, 75b of the first and second minor curves 70a, 70b are disposed mid-way or substantially mid-way between the conjoined inner side 72a/next preceding connecting path segment 64 and the conjoined of inner side 72b/next succeeding connecting path segment 64. The first major curve 68a overlaps the outer side of the second major curve 68b, and the second major curve 68b overlaps the outer side of the first major curve 68a. The first and second minor curves 70a and 70b are arranged side by side. The width W of the entering path portion 66a partly overlaps the width W of the exiting path portion 66b. The widths of both the entering and exiting path portions are between the next preceding and next succeeding connecting path segments.

The path or configuration of the cut 56 in the convoluted path areas 61 thusly involves two major concave curves, i.e. the first major curve 68a and the second major curve 68b, that curve in opposite directions to one another, and two minor concave curves, i.e. the first minor curve 70a and the second minor curve 70b, that curve in opposite directions to one another between the major concave curves, and wherein each curve is followed or next succeeded by one of reverse curvature. In the convoluted path areas 61, the path of cut 56 in the forward direction takes a first, relatively wide curve or bend of relatively gentle concave curvature (first major curve 68a) from the next preceding connecting path segment 64 in the distal direction of the inner member 14, followed by a first, relatively narrower curve or bend of relatively sharper concave curvature (first minor curve 70a) in the proximal direction of the inner member 14 and of reverse curvature from the first, relatively wide curve, followed by a second, relatively narrower curve or bend of the relatively sharper concave curvature (second minor curve 70b) in the proximal direction and of reverse curvature from the first, relatively narrower curve, followed by a second, relatively wide curve or bend of the relatively gentle concave curvature (second major curve 68b) in the distal direction and of reverse curvature from the second, relatively narrower curve to join the next succeeding connecting path segment 64.

Each convoluted path area 61 is joined to the next succeeding convoluted path area 61 by a connecting path segment 64. Each convoluted path area 61 is rotationally spaced from the next preceding convoluted path area 61 in the rotational direction of the cut 56 about the central longitudinal axis 33 of the tubular body 43. In addition, each convoluted path area 61 is offset or spaced longitudinally from the next preceding convoluted path area. In the case of convoluted cut 56, each convoluted path area 61 is longitudinally offset from the next preceding convoluted path area 61 in a longitudinal direction that is toward the terminating end 60 of the cut 56 and toward the distal end or direction of the inner member 14. Each connecting path segment 64 is offset or spaced longitudinally from the next preceding connecting path segment 64 in the longitudinal direction that is toward the terminating end 60 and toward the distal end or direction of the inner member 14. Also, the connecting path segments 64 are in parallel to one another along the tubular body 43.

The convoluted cut 56 can be formed in the tubular body 43 in any suitable manner, preferably by laser cutting the tubular body 43. The radial dimension or thickness of the annular wall of the inner tubular member 14 along the flexible region 42 is the same as the wall thickness 55 of the tubular body 43 along the length portion thereof that is formed with the cut 56, which is the same as the wall thickness of the tubular body 43 along the solid, rigid, uncut segments 50, 52.

In one illustrative referred embodiment, the radius of curvature R1 is or is about 0.02 inch; the radius of curvature R2 is or is about 0.012 inch; the width W is or is about 0.04 inch; the angle B is or is about 20°; the terminating end 60 of the cut 56 is or is about 0.50 inch from the distalmost end surface of the cutting element; the length of the cut region of the tubular body 43 from the starting end 58 to the terminating end 60 of the cut 56 is or is about 1.50 inches; and there are three convoluted path areas 61 in each complete, i.e. 360°, rotational turn or revolution of the cut 56 about the central longitudinal axis 33.

The configuration of convoluted cut 56 in the convoluted path areas 61 forms the wall of tubular body 43 into a pair of complementary, mating and interengaging, opposed first and second hook formations 78a and 78b in the convoluted path areas 61. The first hook formations 78a are all disposed on one side of the convoluted cut 56, and the second hook formations 78b are all disposed on the opposite side of the cut 56. The first hook formation 78a is generally C-shaped or J-shaped in configuration comprising a flared neck 80a and a concavely curved body 82a extending from the neck to a rounded tip 84a. The wider part of the neck 80a merges integrally with the solid portion of the wall of the tubular body 43 that lies between successive rotational turns or revolutions of the cut 56 about the tubular body 43. The neck 80a is defined between the first major curve 68a and the next succeeding connecting path segment 64. The curved body 82a is defined between the first minor curve 70a and the second major curve 68b. The curved body 82a has a longer outer edge of concave curvature along second major curve 68b and a shorter inner side edge of concave curvature along first minor curve 70a, the outer and inner side edges having the same direction of curvature. The tip 84a is defined by the second minor curve 70b between the outer and inner side edges. The second hook formation 78b has the same configuration as the first hook formation 78a but is an inverted mirror image of the first hook formation 78a. The second hook formation 78b includes a flared neck 80b, the wider part of which merges integrally with the solid portion of the tubular body wall that lies between successive rotational turns or revolutions of the cut 56 but on the opposite side of the cut 56 from the neck 80a of first hook formation 78a. The hook formation 78b includes a concavely curved body 82b extending from the neck 80b to a rounded tip 84b. The neck 80b is defined between the second major curve 68b and the next preceding connecting path segment 64. The curved body 82b is defined between the first major curve 68a and the second minor curve 70b. The curved body 82b has a longer outer side edge of concave curvature along first major curve 68a and a shorter inner side edge of concave curvature along second minor curve 70b. The outer and inner side edges of the body 82b have the same direction of curvature, which is reverse from the direction of curvature of the outer and inner side edges of body 82a. The tip 84b is defined by the first minor curve 70a between the outer and inner side edges of the body 82b. The curved body 82a of hook formation 78a curves with a clockwise rotation from the neck 80a in the direction of the starting end 58 of the cut 56 and toward the proximal end or direction of the inner member 14. The curved body 82b of hook formation 78b curves with a clockwise rotation from the neck 80b in the direction opposite or reverse from the hook formation 78a and, therefore, the body 82b curves in the direction of the terminating end 60 of the cut 56 and toward the distal end or direction of the inner member 14. The body 82a of hook formation 78a curves or curls over the tip 84b of hook formation 78b, and the body 82b of hook formation 78b curves or curls over the tip 84a of hook formation 78a in a mating or interengaging fit. The tip 84a of hook formation 78a is mates within the cavity or recess defined by the concave curvature of hook formation 78b and is thusly received between the tip 84b and the neck 80b/body 82b of the hook formation 78b. Conversely, the tip 84b of hook formation 78b mates with the cavity or recess defined by the concave curvature of hook formation 78a and is received between the tip 84a and the neck 80a/body 82a of hook formation 78a. The tip of each hook formation thusly fits and mates with the concave curvature of the opposed hook formation. The hook formations 78a are all unified to one another via the wall of the tubular body 43 disposed on the same side of the cut 56 as the hook formations 78a. The hook formations 78b are all unified to one another via the wall of the tubular body 43 disposed on the opposite side of the cut 56 from the hook formations 78a. The connecting path segments 64 of the convoluted cut 56 are devoid of convoluted path areas 61 and, therefore, are without hook formations 78a, 78b, such that each pair of mating hook formations 78a and 78b is rotationally spaced from the next succeeding pair of mating hook formations about the central longitudinal axis 33 of the tubular body 43. The hook formations 78a have a width equal to the width W of the exiting convoluted path portions 66b, and the hook formations 78b have a width equal to the width W of the entering convoluted path portions 66a.

The cut 56 can be considered "vortical" in the sense that the hook formations 78a, 78b and the path of the cut in the convoluted or vortical path areas 61 are characterized by shapes that resemble a "vortex", i.e. a curving, whirling or swirling shape that forms or defines a cavity toward which something subject to its action is drawn. In each convoluted or vortical path area 61, the vortical path portions 66a, 66b and hook formations 78a, 78b have shapes that resemble vortices rotating in a clockwise direction. The entering path portion 66a rotates in a clockwise direction from the next preceding connecting path segment and the exiting path portion 66b rotates in the clockwise direction from the next succeeding connecting path segment. The first hook formations 78a rotate in the clockwise direction from the necks 80a, and the second hook formations 78b rotate in the clockwise direction from the necks 80b. Furthermore, each hook formation 78a, 78b defines a cavity or recess into which the opposing hook formation is drawn.

The flexible region 42 has numerous advantages including, but not limited to, appropriate rigidity and torsional strength, the ability to transmit torque at bend angles of up to 90°, greater resistance to stretching in the longitudinal direction of the inner member 14, and preservation of the integrity of the internal diameter of the tubular body 43 when transmitting torque during rotation of the inner member 14 within the angled outer tubular member 12. The flexible region 42 has the further advantage of not requiring any additional structural component(s) and/or material(s) over or within the convoluted cut in order to operate effectively as the flexible region for an inner member of an angled rotary tissue cutting instrument. An additional advantage is that the annular wall thickness of the inner member 14 along the flexible region 42 can be better minimized in order to better minimize the external diameter of the inner member and/or to better maximize the internal diameter of the inner member. Also, eliminating the need for additional structural components and/or materials presents the advantage of allowing the flexible region 42 to be produced at lower cost and with greater structural simplicity for a reduced risk of operational problems. Although the flexible region 42 does not require any additional structural component(s) over the convoluted cut, it is possible to provide a very thin-walled sleeve or sheath over the cut region of the tubular body while retaining the aforementioned advantages. The flexible region 42 is especially well-suited for use with an angled outer tubular member 12 having a bend angle A of up to 90°.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. An angled rotary tissue cutting instrument for cutting anatomical tissue, comprising
an elongate angled outer tubular member having a distal end, a longitudinal internal passage, an open proximal end communicating with said passage, an angled region between said distal end and said proximal end, and an opening in said distal end communicating with said passage; and
a flexible inner member for being rotatably disposed within said outer tubular member, said inner member having a distal end, a proximal end, a tubular body between said distal end of said inner member and said proximal end of said inner member, a cutting element at said distal end of said inner member, said cutting element being exposed from said opening to cut anatomical tissue when said inner member is rotatably disposed within said outer tubular member, and a flexible region for being disposed within said angled region to transmit torque to rotate said cutting element while conforming to the configuration of said angled region when said inner member is rotated within said outer tubular member, said tubular body having a central longitudinal axis and a cylindrical wall with an external diameter surface, an internal diameter surface, and a wall thickness between said external diameter surface and said internal diameter surface, said flexible region consisting of a convoluted cut in said tubular body extending entirely through said wall thickness, said convoluted cut having a single starting end on said tubular body and a single terminating end on said tubular body, said convoluted cut being continuous from said starting end to said terminating end, said convoluted cut following a winding path extending longitudinally along said tubular body and extending in a rotational direction about said central longitudinal axis in a forward direction of said convoluted cut from said starting end to said terminating end, said convoluted cut consisting of a plurality of convoluted path areas rotationally spaced about said central longitudinal axis along said winding path between said starting end and said terminating end and a plurality of connecting path segments alternating individually with said convoluted path areas such that a single connecting path segment is disposed between successive convoluted path areas in said forward direction, said connecting path segments extending in said rotational direction along said tubular body, said convoluted cut following a convoluted path in said convoluted path areas in said forward direction of said cut comprising a first major curve of concave curvature extending from a next preceding one of said connecting path segments in a lateral direction away from said next preceding one of said connecting path segments, a first minor curve of concave curvature reverse from said curvature of said first major curve extending from said first major curve in an opposite lateral direction toward said next preceding one of said connecting path segments, a second minor curve of concave curvature reverse from said curvature of said first minor curve extending from said first minor curve in said opposite lateral direction, and a second major curve of concave curvature reverse from said curvature of said second minor curve extending from said second minor curve in said lateral direction to a next succeeding one of said connecting path segments, said first minor curve being within said second major curve and being spaced from said second major curve in a direction radial to said second major curve, said second minor curve being within said first major curve and being spaced from said first major curve in a direction radial to said first major curve, said convoluted cut in said tubular body imparting sufficient strength and rigidity to said flexible region for said flexible region to transmit torque to rotate said cutting element to cut anatomical tissue.

2. The angled rotary tissue cutting instrument recited in claim 1 wherein said major curves have a radius of curvature, and said minor curves have a radius of curvature about 60% of said radius of curvature of said major curves.

3. The angled rotary tissue cutting instrument recited in claim 1 wherein said connecting path segments are all disposed at the same acute angle to a plane perpendicular to said central longitudinal axis of said tubular body.

4. The angled rotary tissue cutting instrument recited in claim 3 wherein said connecting path segments are parallel to one another along said tubular body.

5. The angled rotary tissue cutting instrument recited in claim 1 wherein said lateral direction and said opposite lateral direction are transverse to said next preceding one of said connecting path segments and to said next succeeding one of said connecting path segments.

6. The angled rotary tissue cutting instrument recited in claim 5 wherein said lateral direction is toward said distal end of said inner member and said opposite lateral direction is toward said proximal end of said inner member.

7. The angled rotary tissue cutting instrument recited in claim 6 wherein said lateral direction is toward said terminating end of said convoluted cut and said opposite lateral direction is toward said starting end of said convoluted cut.

8. An angled rotary tissue cutting instrument for cutting anatomical tissue, comprising
an elongate angled outer tubular member having a distal end, a longitudinal internal passage, an open proximal end communicating with said passage, an angled region between said distal end and said proximal end, and an opening in said distal end communicating with said passage; and
a flexible inner member for being rotatably disposed within said outer tubular member, said inner member having a distal end, a proximal end, a tubular body between said distal end of said inner member and said proximal end of said inner member, a cutting element at said distal end of said inner member, said cutting element being exposed from said opening to cut anatomical tissue when said inner member is rotatably disposed within said outer tubular member, and a flexible region for being disposed within said angled region to transmit torque to rotate said cutting element while conforming to the configuration of said angled region when said inner member is rotated within said outer tubular member, said tubular body having a central longitudinal axis and a cylindrical wall with an external diameter surface, an internal diameter surface, and a wall thickness between said external diameter surface and said internal diameter surface, said flexible region consisting of a convoluted cut in said tubular body extending entirely through said wall thickness, said convoluted cut having a single starting end on said tubular body and a single terminating end on said tubular body, said convoluted cut being continuous from said starting end to said terminating end said convoluted cut following a winding path extending longitudinally along said tubular body and extending in a rotational direction about said central longitudinal axis in a forward direction of said convoluted cut from said starting end to said terminating end, said convoluted cut consisting of a plurality of convoluted path areas rotationally spaced about said central longitudinal axis along said winding path between said starting end and said terminating end and a plurality of connecting path segments alternating with said convoluted path areas, said connecting path segments extending in said rotational direction along said tubular body and being devoid of said convoluted path areas, said convoluted cut following a convoluted path in said convoluted path areas consisting of a first major curve of concave curvature having an inner side continuous with a next preceding one of said connecting path segments and having an outer side spaced from said next preceding one of said connecting path segments, a first minor curve of reverse concave curvature to said first major curve and having an outer side continuous with said outer side of said first major curve and having an inner side between said outer side of said first minor curve and said next preceding one of said connecting path segments, a second minor curve of concave curvature curving in the same direction as said first major curve and being within said first major curve in spaced relation to said first major curve, said second minor curve having an inner side continuous with said inner side of said first minor curve and having an outer side between said inner side of said second minor curve and said next preceding one of said connecting path segments, and a second major curve of concave curvature curving in the same direction as said first minor curve and having an outer side continuous with said outer side of said second minor curve and having an inner side continuous with a next succeeding one of said connecting path segments, said first minor curve being within said second major curve in spaced relation to said second major curve, said convoluted cut in said tubular body imparting sufficient strength and rigidity to said flexible region for said flexible region to transmit torque to rotate said cutting element to cut anatomical tissue.

9. The angled rotary tissue cutting instrument recited in claim 8 wherein said connecting path segments are all disposed at the same acute angle with a plane perpendicular to said central longitudinal axis of said tubular body and extend in said forward direction of said cut with a slant toward said proximal end of said inner member.

10. The angled rotary tissue cutting instrument recited in claim 8 wherein said convoluted path areas have an entering convoluted path portion formed by said first major curve and said first minor curve, and an exiting convoluted path portion formed by said second minor curve and said second major curve, and said exiting convoluted path portion is an inverted mirror image of said entering convoluted path portion.

11. The angled rotary tissue cutting instrument recited in claim 8 wherein said first and second major curves have a radius of curvature of about 0.02 inch and said first and second minor curves have a radius of curvature of about 0.012 inch.

12. The angled rotary tissue cutting instrument recited in claim 11 wherein said convoluted path portions each have a width in a direction parallel to said central longitudinal axis of said tubular body of about 0.04 inch.

13. An angled rotary tissue cutting instrument for cutting anatomical tissue, comprising
an elongate outer tubular member having a distal end, a longitudinal internal passage, an open proximal end communicating with said passage, an angled region between said distal end and said proximal end, and an opening in said distal end communicating with said passage; and
a flexible inner member for being rotatably disposed within said outer tubular member, said inner member having a distal end, a proximal end, a tubular body between said distal end of said inner member and said proximal end of said inner member, a cutting element at said distal end of said inner member, said cutting element being exposed from said opening to cut anatomical tissue when said inner member is rotatably disposed within said outer tubular member, and a flexible region for being disposed within said angled region to transmit torque to rotate said cutting element while conforming to the configuration of said angled region when said inner member is rotated within said outer tubular member, said tubular body having a central longitudinal axis and a cylindrical wall with an external diameter surface, an internal diameter surface, and a wall thickness between said external diameter surface and said internal diameter surface, said flexible region consisting of a convoluted cut in said tubular body extending entirely through said wall thickness, said convoluted cut having a single starting end on said tubular body and a single terminating end on said tubular body, said convoluted cut following a winding path extending longitudinally along said tubular body and extending in a rotational direction about said central longitudinal axis in a forward direction of said convoluted cut from said starting end to said terminating end, said convoluted cut consisting of a plurality of convoluted path areas rotationally spaced about said central longitudinal axis along said winding path between said starting end and said terminating end and a plurality of connecting path segments alternating with said convoluted path areas, said convoluted cut being continuous through said convoluted path areas and following a convoluted configuration in each of said convoluted path areas forming a single pair of opposed hook formations in said wall of said tubular body in each of said convoluted path areas, each of said pairs of opposed hook formations consisting of a first hook formation of concave curvature and a second hook formation of concave curvature reverse from said curvature of said first hook formation, said first and second hook formations of each of said pairs of opposed hook formations being interengaged with one another in a complementary, mating fit, each of said pairs of opposed hook formations being disposed between a next preceding one of said connecting path segments and a next succeeding one of said connecting path segments, said connecting path segments extending in said rotational direction at a nonperpendicular angle to said central longitudinal axis and being devoid of said hook formations, said convoluted cut in said tubular body impartinq sufficient strength and rigidity to said flexible region for said flexible region to transmit torque to rotate said cutting element to cut anatomical tissue.

14. The angled rotary tissue cutting instrument recited in claim 13 wherein said convoluted cut is continuous from said starting end to said terminating end.

15. The angled rotary tissue cutting instrument recited in claim 13 wherein said first hook formations are disposed on a first side of said convoluted cut and curve with a clockwise rotation in a direction toward said starting end, and said second hook formations are disposed on a second side of said convoluted cut opposite from said first hook formations and curve with a clockwise rotation toward said terminating end.

16. The angled rotary tissue cutting instrument recited in claim 15 wherein said first hook formations include a neck integral with said cylindrical wall of said tubular body on said first side of said convoluted cut and a concavely curving body extending from said neck to a rounded tip, said second hook formations are an inverted mirror image of said first hook formations and include a neck integral with said cylindrical wall of said tubular body on said second side of said convoluted cut and a concavely curving body extending from neck to a rounded tip, said tips of said first hook formations mating with said concave curvature of said second hook formations and said tips of said second hook formations mating with said concave curvature of said first hook formations.

17. The angled rotary tissue cutting instrument recited in claim 16 wherein said curving bodies of said first hook formations have a longer outer side edge of concave curvature and a shorter inner side edge of concave curvature in the same direction as said concave curvature of said outer side edge, said curving bodies of said second hook formations have a longer outer side edge of concave curvature reverse from said concave curvature of said outer side edge of said first hook formations, and a shorter inner side edge of concave curvature in the same direction as said concave curvature of said outer side edge of said second hook formations.

18. The angled rotary tissue cutting instrument recited in claim 17 wherein said outer side edges have a radius of curvature of 0.02 inch and said inner side edges have a radius of curvature of 0.012 inch.

19. The angled rotary tissue cutting instrument recited in claim 18 wherein said first and second hook formations each have a width in a direction parallel to said central longitudinal axis of 0.04 inch.

* * * * *